United States Patent
Koktzoglou

(10) Patent No.: US 10,413,213 B2
(45) Date of Patent: Sep. 17, 2019

(54) SYSTEM AND METHOD FOR HYBRID RADIOFREQUENCY LABELING FOR MAGNETIC RESONANCE IMAGING

(75) Inventor: Ioannis Koktzoglou, Des Plaines, IL (US)

(73) Assignee: NORTHSHORE UNIVERSITY HEALTHSYSTEM, Evanston, IL (US)

( * ) Notice: Subject to any disclaimer, the term of this patent is extended or adjusted under 35 U.S.C. 154(b) by 1120 days.

(21) Appl. No.: 13/111,724

(22) Filed: May 19, 2011

(65) Prior Publication Data

US 2012/0296193 A1 Nov. 22, 2012

(51) Int. Cl.
| | |
|---|---|
| *A61B 5/055* | (2006.01) |
| *A61B 5/02* | (2006.01) |
| *G01R 33/563* | (2006.01) |
| *A61B 5/026* | (2006.01) |

(52) U.S. Cl.
CPC .......... *A61B 5/055* (2013.01); *A61B 5/02007* (2013.01); *G01R 33/5635* (2013.01); *A61B 5/0263* (2013.01)

(58) Field of Classification Search
CPC ... A61B 5/055; A61B 5/02007; A61B 5/0263; G01R 33/5635
See application file for complete search history.

(56) References Cited

U.S. PATENT DOCUMENTS

| | | | | |
|---|---|---|---|---|
| 6,564,080 B1* | 5/2003 | Kimura | ................ | A61B 5/0263 324/307 |
| 6,717,405 B2* | 4/2004 | Alsop | ........................... | 324/306 |
| 7,627,360 B2* | 12/2009 | Kimura | ........................ | 600/419 |
| 2004/0204643 A1* | 10/2004 | Jesmanowicz | ... | G01R 33/56341 600/410 |
| 2008/0061780 A1* | 3/2008 | Yamada et al. | ................ | 324/309 |
| 2008/0281181 A1* | 11/2008 | Manzione et al. | ............. | 600/407 |
| 2009/0005670 A1* | 1/2009 | Ichinose | .......... | G01R 33/56308 600/410 |
| 2009/0143666 A1* | 6/2009 | Edelman | ................ | A61B 5/055 600/410 |

(Continued)

OTHER PUBLICATIONS

Garcia et al., Pseudo-continuous Flow Driven Adiabatic Inversion for Arterial Spin Labeling, Proc. Intl. Soc. Mag. Reson. Med. 13, 2005.*

(Continued)

*Primary Examiner* — Bo Joseph Peng
(74) *Attorney, Agent, or Firm* — Quarles & Brady LLP

(57) ABSTRACT

A system and method is provided for magnetic resonance angiography (MRA) that includes applying a first labeling pulse sequence to a first labeling region having a first portion of a vasculature of a subject extending through the first labeling region to label spins moving within the first labeling region. A second labeling pulse sequence is applied to a second labeling region having a second portion of a vasculature of the subject extending through the second labeling region to label spins moving within the second labeling region. The first and second labeling pulse sequences include different labeling techniques. An imaging pulse sequence is applied to an imaging region having a third portion of a vasculature of the subject extending through the imaging region that is displaced from the first and second labeling region to acquire imaging data from the spins labeled by the first labeling pulse sequence and the second labeling pulse sequence. An MRA image is reconstructed of at least the third portion of the vasculature of the subject from the medical imaging data.

16 Claims, 5 Drawing Sheets

(56) References Cited

U.S. PATENT DOCUMENTS

| | | | |
|---|---|---|---|
| 2009/0149733 A1* | 6/2009 | Guenther | A61B 5/0263 600/410 |
| 2009/0309592 A1* | 12/2009 | Furudate | 324/306 |
| 2010/0198053 A1* | 8/2010 | Miyazaki et al. | 600/419 |

OTHER PUBLICATIONS

Wong et al, A Theoretical and Experimental Comparison of Continuous and Pulsed Arterial Spin Labeling Techniques for Quantitative Perfusion Imaging, MRM 40:348-355 (1996).

Dai et al, Modified Pulsed Continuous Arterial Spin Labeling for Labeling of a Single Artery, MRM 64:975-982 (2010).

Robson et al, Time-resolved Vessel-selective Digital Subtraction MR Angiography of the Cerebral Vasculature with Arterial Spin Labeling, Radiology, vol. 257, No. 2, Nov. 2010.

Helle et al, Superselective Pseudocontinuous Arterial Spin Labeling, MRM 64:777-786 (2010).

Wong, Eric C, Vessel-Encoded Arterial Spin-Labeling Using Pseudocontinuous Tagging, MRM 58:1086-1091 (2007).

Wu et al, A Theoretical and Experimental Investigation of the Tagging Efficiency of Pseduocontinuous Arterial Spin Labeling, MRM 58:1020-1027 (2007).

Dai et al, Continuous Flow-Drive Inversion for Arterial Spin Labeling Using Pulsed Radio Frequency and Gradient Fields, MRM 60:1488-1497 (2008).

Koktzoglou et al, Star and Starfire for Flow-Dependent and Flow-Independent Noncontrast Carotid Angiography, MRM 61:117-124 (2009).

* cited by examiner

SYSTEM AND METHOD FOR HYBRID RADIOFREQUENCY LABELING FOR MAGNETIC RESONANCE IMAGING

STATEMENT REGARDING FEDERALLY SPONSORED RESEARCH

This invention was made with Government support under Grant No. R01 HL096916 awarded by the National Institutes of Health. The Government has certain rights in this invention.

CROSS-REFERENCE TO RELATED APPLICATIONS

N/A

FIELD OF THE INVENTION

The invention relates to a system and method for performing magnetic resonance imaging and, more particularly, to a system and method for acquiring data suitable for arterial spin labeling (ASL).

BACKGROUND OF THE INVENTION

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance ("NMR") phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

Magnetic resonance angiography (MRA) and, related imaging techniques, such as perfusion imaging, use the NMR phenomenon to produce images of the human vasculature or physiological performance related to the human vasculature. There are three main categories of techniques for achieving the desired contrast for the purpose of MR angiography. The first general category is typically referred to as contrast enhanced (CE) MRA. The second general category is phase contrast (PC) MRA. The third general category is time-of-flight (TOF) or tagging-based MRA.

To perform CE MRA, a contrast agent, such as gadolinium, is injected into the patient prior to the magnetic resonance (MR) angiogram to enhance the diagnostic capability of the MR angiogram. Perfusion imaging is employed to assess the viability of tissues. A contrast agent is administered to the subject and a series of MR images are acquired as the contrast agent perfuses into the tissues of interest. From this series of contrast-enhanced MR images hemodynamic parameters such as blood flow, blood volume, and mean transit time may be computed.

While CE MRA is a highly effective means for noninvasively evaluating the vascular and physiological performance, for example, by studying perfusion, the technique suffers from several additional drawbacks. First, the contrast agent that must be administered to enhance the blood vessel carries a significant financial cost. Second, contrast agents such as gadolinium have recently been shown to be causative of a debilitating and potentially fatal disorder called nephrogenic systemic fibrosis (NSF). Third, CE MRA, may not provide accurate or sufficient hemodynamic information, so that it is not always feasible to determine if a stenosis is hemodynamically significant or to asses the perfusion in a clinically useful manner.

Phase contrast (PC) MRA is largely reserved for the measurement of flow velocities and imaging of veins. Phase contrast sequences are the basis of MRA techniques utilizing the change in the phase shifts of the flowing protons in the region of interest to create an image. Spins that are moving along the direction of a magnetic field gradient receive a phase shift proportional to their velocity. Specifically, in a PC MRA pulse sequence, two data sets with a different amounts of flow sensitivity are acquired. This is usually accomplished by applying gradient pairs, which sequentially dephase and then rephase spins during the sequence. The first data set is acquired using a "flow-compensated" pulse sequence or a pulse sequence without sensitivity to flow. The second data set is acquired using a pulse sequence designed to be sensitive to flow. The amount of flow sensitivity is controlled by the strength of the bipolar gradient pairs used in the pulse sequence because stationary tissue undergoes no effective phase change after the application of the two gradients, whereas the different spatial localization of flowing blood is subjected to the variation of the bipolar gradient. Accordingly, moving spins experience a phase shift. The raw data from the two data sets are subtracted to yield images that illustrate the phase change, which is proportional to spatial velocity. To perform PC MRA pulse sequences, a substantial scan time is generally required and the operator must set a velocity-encoding sensitivity, which varies unpredictably depending on a variety of clinical factors.

Fortunately, TOF imaging techniques do not require the use of a contrast agent and do not rely on potentially-precarious velocity encoding sensitivities. Contrary to CE-MRA, which relies on the administered contrast agent to provide an increase in measured MR signal, TOF MRA relies on the inflow of blood into an imaging volume to increase the signal intensity of the vasculature as compared to the stationary background tissues. This is achieved by the application of a number of RF excitation pulses to the imaging volume that cause the magnetization of the stationary background tissues to reach a saturation value. Since inflowing blood entering the imaging volume is not exposed to the same number of RF excitation, it will provide higher MR signal intensity than the background tissue. The differences between the signal intensity of the stationary background tissues and the inflowing blood thus provide a contrast mechanism exploited by TOF MRA.

In an effort to increase contrast attributable to the relatively small signal levels or weight particular signals, for example, those attributable to cerebral blood flow (CBF) or another measurable mechanism, various "tagging" or "labeling" methods have been developed. One such method is referred to as the arterial spin labeling (ASL) family of techniques. These techniques have been used to detect and provide a quantitative measure of neuronal activity.

Existing RF labeling preparations for ASL-based imaging can generally be grouped into two classes. The first class is typically referred to as "pulsed RF labeling" and the second class is typically referred to as "continuous RF labeling" or "pseudo-continuous RF labeling." Pulsed RF labeling techniques apply one or a few RF pulses, (usually of the adiabatic type) to a tissue location of interest prior to image acquisition. In the case of angiography, these pulsed RF labeling techniques are typically applied to upstream or inflowing vascular spins. On the other hand, continuous (or pseudo-continuous) RF labeling techniques apply either a continuous level of RF energy or, in the case of "pulsed continuous" or "pseudo-continuous" RF labeling preparations, a train of distinct RF pulses to a region containing upstream or inflowing vascular spins. Compared with pulsed RF labeling preparations, continuous (or pseudo-continuous) RF labeling preparations typically provide larger signal-to-noise ratios (SNR) from flowing spins, but impart a large amount of RF energy which may exceed that which is clinically desired or acceptable under government regulations, especially at high magnetic field strengths.

In MR angiographic applications, for instance, the disadvantage of pulsed RF labeling compared with continuous (or pseudo-continuous) RF labeling is lower SNR in the blood vessels being imaged. The disadvantage of continuous (or pseudo-continuous) RF labeling is high RF energy deposition which may exceed specific absorption rate (SAR) limits, especially at high magnetic field strengths. A major disadvantage of pseudo-continuous RF labeling is that inflowing vascular spins are not labeled after the train of labeling RF pulses ends, which reduces SNR in vascular segments near the labeling region. Compared with pulsed RF labeling, additional disadvantages of pseudo-continuous RF labeling include increased labeling sensitivity to imperfections in the main magnetic field ($B_0$) or RF field ($B_1$) and blood velocity.

Therefore, it would be desirable to have a system and method for performing angiographic studies using MRI systems without the drawbacks presented by CE-MRA or PC-MRA techniques. Furthermore, it would be desirable to have a system and method for MR angiography that allows the user to achieve a desirable vascular SNR while adhering to regulated SAR limits.

SUMMARY OF THE INVENTION

The present invention provides a system and method for producing an angiogram with a magnetic resonance imaging (MRI) system that combines pulsed and continuous (or pseudo-continuous) radiofrequency (RF) labeling preparations to yield increased SNR over traditional pulsed RF labeling techniques and controls SAR and other undesirable constraints with flexibility not provided by continuous (or pseudo-continuous) RF labeling techniques. Specifically, the present innovation provides a "hybrid" RF spin-labeling preparation that consists of at least two RF labeling pulse sequence modules applied to distinct, but potentially overlapping labeling regions at different times, followed by an imaging pulse sequence applied to a region of interest (ROI) that is distinct from the different labeling regions.

In accordance with one aspect of the invention, a method for acquiring a magnetic resonance angiography (MRA) image of a portion of a vasculature of a subject using a magnetic resonance imaging system is disclosed that includes applying a first labeling pulse sequence to a first labeling region having a first portion of a vasculature of a subject extending through the first labeling region to label spins within the first labeling region. A second labeling pulse sequence is applied to a second labeling region having a second portion of a vasculature of the subject extending through the second labeling region to label spins within the second labeling region. The first and second labeling pulse sequences include different spin-labeling labeling techniques. An imaging pulse sequence is applied to an imaging region having a third portion of a vasculature of the subject extending through the imaging region that is displaced from the first and second labeling region to acquire imaging data from the spins labeled by the first labeling pulse sequence module and the second labeling pulse sequence module. An MRA image is reconstructed of at least the third portion of the vasculature of the subject from the medical imaging data.

In accordance with another aspect of the invention, a magnetic resonance imaging (MRI) system is disclosed that includes a magnet system configured to generate a polarizing magnetic field about at least a portion of a subject arranged in the MRI system, a plurality of gradient coils configured to apply a gradient field to the polarizing magnetic field, and a radio frequency (RF) system configured to apply an excitation field to the subject and acquire MR image data therefrom. A computer system is provided that is programmed to apply a first labeling pulse sequence to a first labeling region having a first portion of a vasculature of a subject extending through the first labeling region to label spins within the first labeling region. The computer system is further programmed to apply a second labeling pulse sequence to a second labeling region having a second portion of a vasculature of the subject extending through the second labeling region to label spins within the second labeling region. The first and second labeling pulse sequences include different spin-labeling techniques. The computer system is also programmed to apply an imaging pulse sequence to an imaging region having a third portion of a vasculature of the subject extending through the imaging region that is displaced from the first and second labeling region to acquire imaging data from the spins labeled by the first labeling pulse sequence module and the second labeling pulse sequence module and reconstructing an MRA image of at least the third portion of the vasculature of the subject from the medical imaging data.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
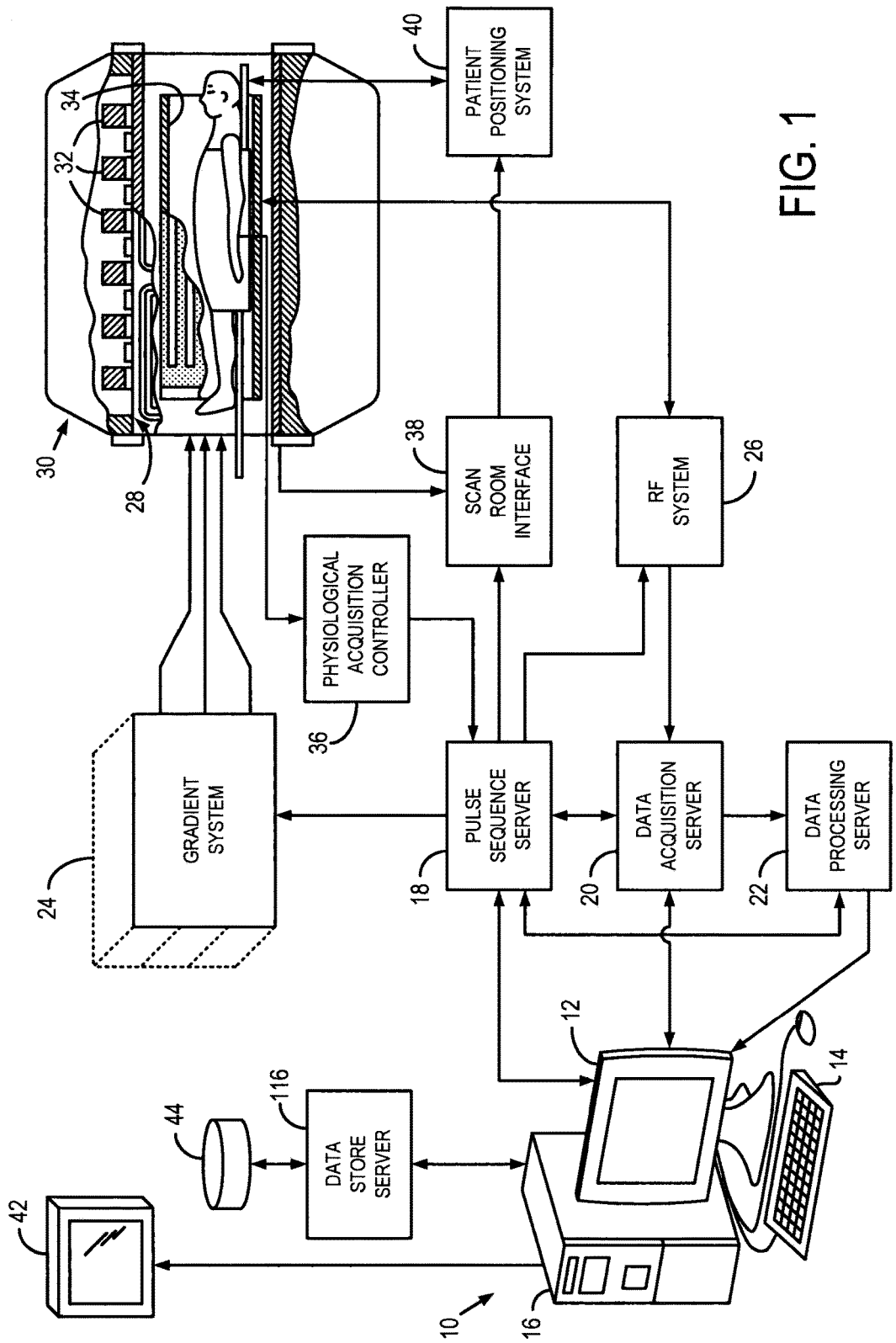
FIG. 1 is a block diagram of an MRI system for use with the present invention.

Referring particularly to FIG. 1, the invention is employed in an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system.

The workstation 10 is coupled to, for example, four servers, including a pulse sequence server 18, a data acquisition server 20, a data processing server 22, and a data store server 23. In one configuration, the data store server 23 is performed by the workstation processor 16 and associated disc drive interface circuitry and the remaining three servers 18, 20, 22 are performed by separate processors mounted in a single enclosure and interconnected using a backplane bus. The pulse sequence server 18 employs a commercially available microprocessor and a commercially available communication controller. The data acquisition server 20 and data processing server 22 both employ commercially available microprocessors and the data processing server 22 further includes one or more array processors based on commercially available processors.

The workstation 10 and each processor for the servers 18, 20, 22 are connected to a communications network. This network conveys data that is downloaded to the servers 18, 20, 22 from the workstation 10 and conveys data that is communicated between the servers 18, 20, 22 and between the workstation 10 and the servers 18, 20, 22. In addition, a high speed data link is typically provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$, and $G_z$ used for position encoding NMR signals. The gradient coil assembly 28 forms part of a magnet assembly 30, which includes a polarizing magnet 32 and a whole-body RF coil 34.

The RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered, and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase, and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector that detects and digitizes the in-phase (I) and quadrature (Q) components of the received NMR signal. The magnitude of the received NMR signal may thus be determined at any sampled point by the square root of the sum of the squares of the I and Q components.

The pulse sequence server 18 also optionally receives patient data from a physiological acquisition controller 36. The controller 36 receives signals from a number of different sensors connected to the patient, such as ECG signals from electrodes or respiratory signals from a bellows.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner by run-time programs. The description components for a scan prescription are downloaded from the workstation 10 in the form of objects. The pulse sequence server 18 contains programs that receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans, the data acquisition server 20 does little more than pass the acquired NMR data to the data processor server 22. However, in scans that require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. Furthermore, the data acquisition server 20 may be employed to process NMR signals used to detect the arrival of contrast agent in an MRA scan. In all these examples the data acquisition server 20 acquires NMR data and processes it in real-time to produce information that is used to control the scan.

The data processing server 22 receives NMR data from the data acquisition server 20 and processes it in accordance with description components downloaded from the workstation 10. Such processing may include, for example, Fourier transformation of raw k-space NMR data to produce two or three-dimensional images, the application of filters to a reconstructed image, the performance of a backprojection image reconstruction of acquired NMR data, the calculation of functional MR images, the calculation of motion or flow images, and the like.

Images reconstructed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
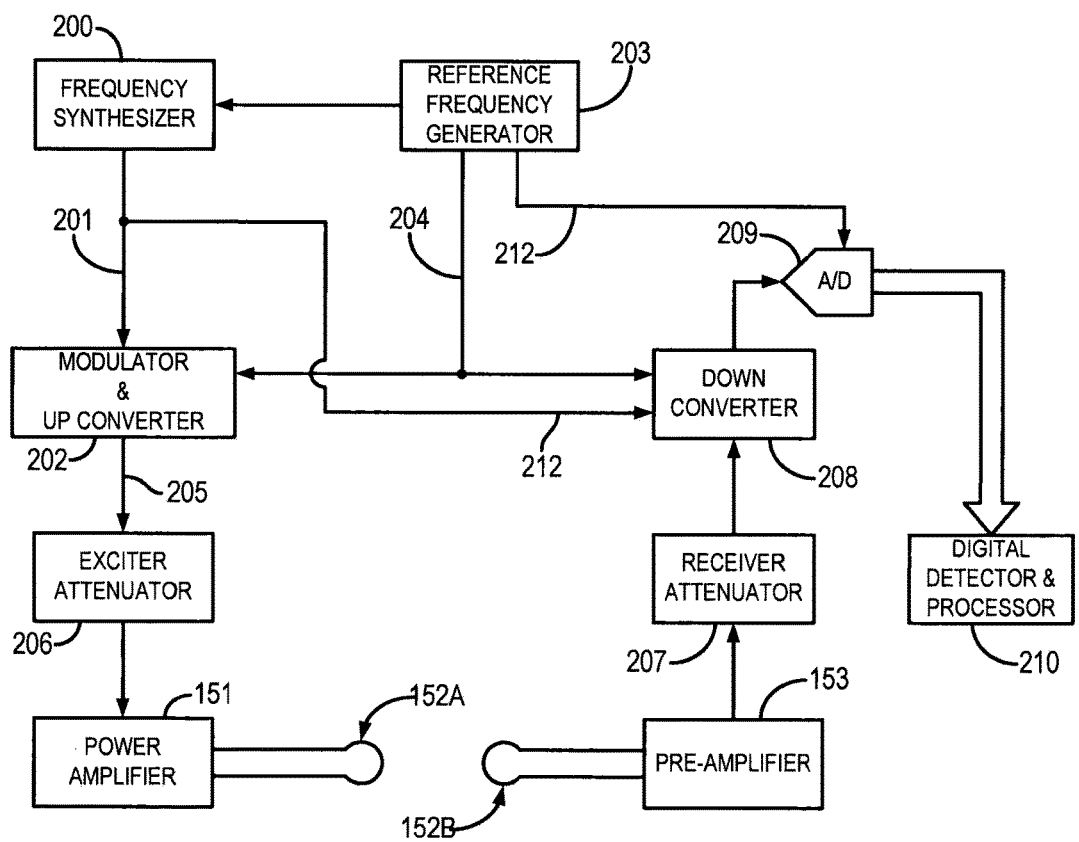
FIG. 2 is a schematic representation of a transceiver system for use with the MRI system of FIG. 1.

As shown in FIG. 1, the RF system 26 may be connected to the whole body RF coil 34, or as shown in FIG. 2, a transmitter section of the RF system 26 may connect to one RF coil 151A and its receiver section may connect to a separate RF receive coil 151B. Often, the transmitter section is connected to the whole body RF coil 34 and each receiver section is connected to a separate local coil 151B.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may, be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the RF coil 151A.

Referring still to FIG. 2, the signal produced by the subject is received by the receiver coil 152B and applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high frequency signal is down converted in a two step process by a down converter 208 that first mixes the NMR signal with the carrier signal on line 201 and then mixes the resulting difference signal with a reference signal on line 204. The down converted NMR signal is applied to the input of an analog-to-digital (ND) converter 209 that samples and digitizes the analog signal and applies it to a digital detector and signal processor 210 to produce the I values and Q values corresponding to the received signal. As described above, the resulting stream of digitized I and Q values of the received signal are output to the data acquisition server 20 of FIG. 1. The reference signal, as well as the sampling signal applied to the ND converter 209, is produced by a reference frequency generator 203.

Figure 3:
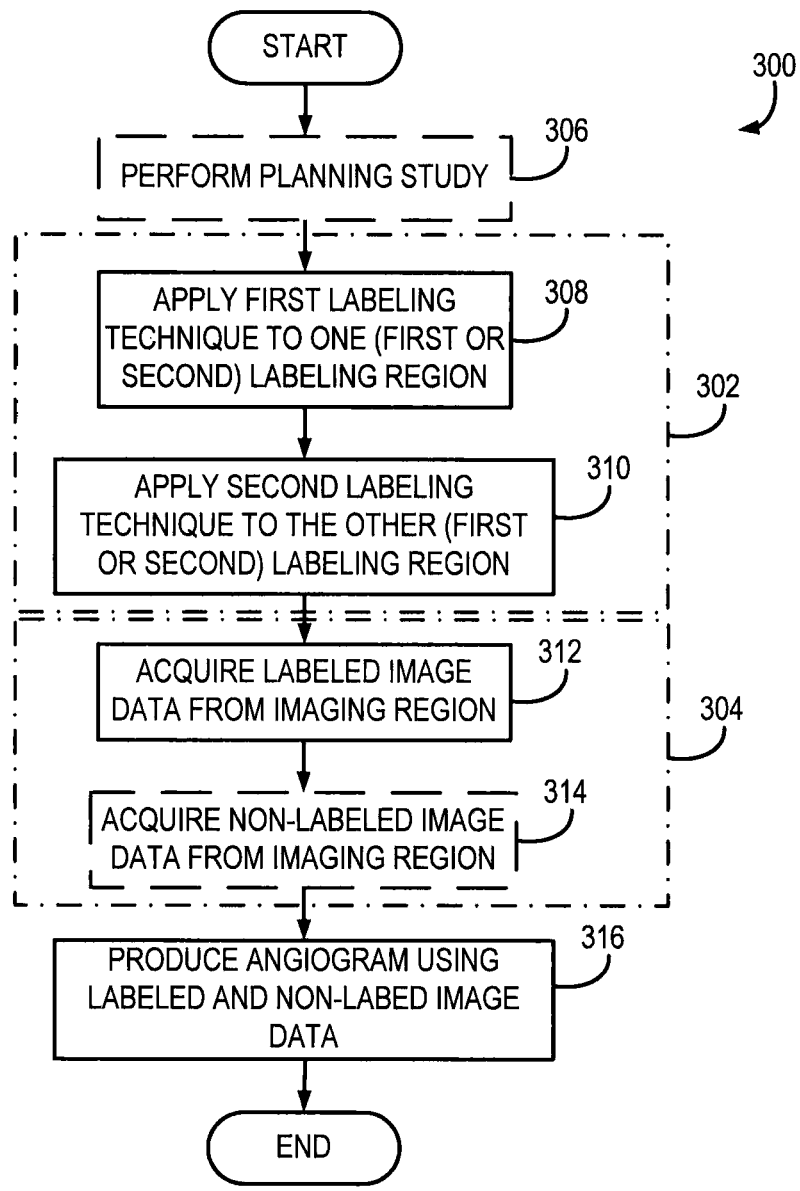
FIG. 3 is a flow chart of the steps performed in accordance with one exemplary implementation of the present invention.

Referring to FIG. 3, a method 300 in accordance with the present invention can be conceptualized as including a labeling module 302 that employs principles of arterial spin labeling (ASL), followed by an imaging module 304. The labeling module 302 begins with an optional planning study at process block 306. The planning study may include imaging the subject to determine an anatomical location (blood vessel, organ, bone, joint) or physiological parameter (blood velocity) within the subject Alternatively, the planning study may include evaluating the subject without imaging, in which case generalized planning properties may be used to guide the labeling module 302 and acquisition module 304. In either case, when any pre-planning is complete, the user will have identified an imaging region and first and second labeling regions so that the labeling module 302 can begin.

Figure 4A:
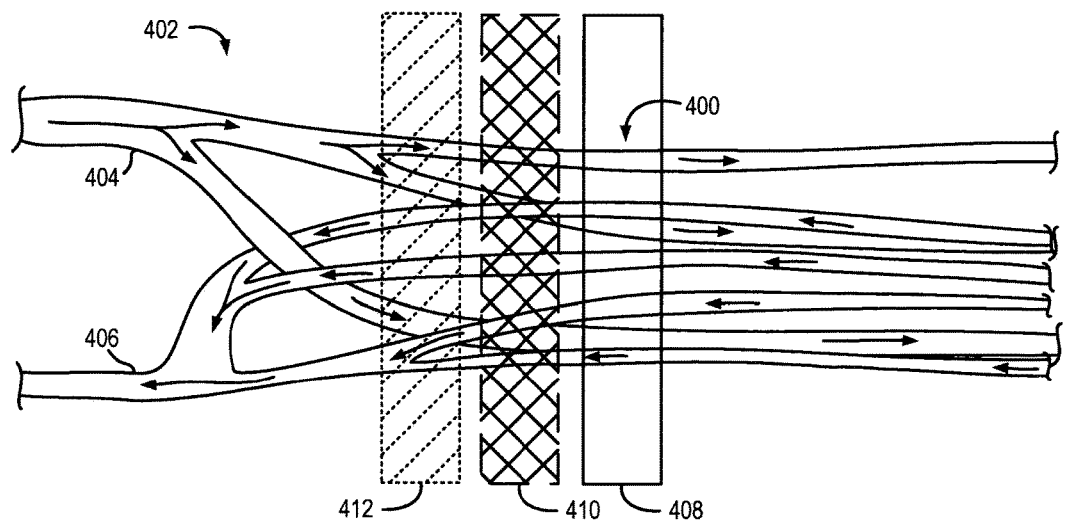
FIGS. 4A-4C are a schematic diagrams providing an example of one spatial-temporal plan for performing a spin labeling imaging process in accordance with the present invention.

Referring to FIGS. 3 and 4A-4D, the performance of the labeling module 302 and imaging module 304 will be described. Specifically, as illustrated in FIG. 4A, a region of interest (ROI) 400 is identified by the user that extends along a portion of a vasculature 402 of the subject. As illustrated, the vasculature 402 and thus, the region of interest 400, includes both arteries 404 and veins 406. As illustrated by arrows superimposed on the arteries 404 and veins 406, blood, and thus the spins contained therein, flowing within the arteries 404 and veins 406 moves in generally opposing directions. As will be explained, this opposing flow can be used in the present invention to selectively acquire images of only the arteries 404 or only the veins 406 (or, if desired, both arteries 404 and veins 406). In the example described hereinafter, the desired images to be acquired are to include only the arteries 404.

With the ROI 400 identified by the user, an imaging region 408 is designated that covers the ROI 400. It is noted that the imaging region 408, depending upon clinical application, may be a two-dimensional (2D) slice or a three-dimensional (3D) volume. Again, in the illustrated example, the desired images to be acquired are to include only the arteries 404. Accordingly, a first labeling region 410 is designated "upstream" (based on arterial flow) of the imaging region 408, such that arterial blood and the spins contained with arterial blood flows from the first labeling region 410 to the imaging region 408. Furthermore, a second labeling region 412 is designated further "upstream" (based on arterial flow) of the imaging region 408 and the first labeling region 410, such that arterial blood and the spins contained with arterial blood flows from the second labeling region 412 to the first labeling region 410 and, then, to the imaging region 408. As will be described, although FIGS. 4A-4D illustrate the use of a first labeling region 410 and a second labeling region 412, it is contemplated that more than two labeling regions may be utilized. In a conceptually similar perspective, it is contemplated that sub-regions of the labeling regions may be designated. Similarly, it is contemplated that the labeling regions and/or the imaging region may, at least partially, overlap.

Once the location and relative positions of the imaging region 408 and first and second labeling regions 410, 412 are identified, referring to FIGS. 3 and 4A, the labeling module 302 can commence. The labeling module 302 begins at process block 308 by performing a first labeling technique that is applied to one of the labeling regions 410, 412. For purposes of the following example, and not by way of limitation, the present example will be described with respect to the first labeling technique being applied to the first labeling region 410. In accordance with this example, at process block 310, a second labeling technique is applied to the other labeling region, here, the second labeling region 412.

It is noted that, as illustrated in FIG. 4A, the first labeling region 410 and the second labeling region 412 are positioned in spatially separate regions about the vasculature 402. As illustrated, the first labeling region 410 and the second labeling region 412 may be entirely spatially separated or, in some cases, may share an overlapping portion. Furthermore, it is noted that the first labeling region 410 and the second labeling region 412 are spatially separated (at least partially) from the ROI 400 and imaging region 408. Nonetheless, depending on the desired image contrast, the labeling and imaging regions 410, 412, and 400 may overlap.

In addition to designing the first labeling region 410 and the second labeling region 412 to cover at least partially disparate spatial locations along the vasculature, the present invention advantageously utilizes two, different labeling techniques. That is, as described above, a first labeling technique is applied at process block 308 and a second labeling technique is applied at process block 310 and it is contemplated that these labeling techniques differ. As will be described, by utilizing multiple (at least two) labeling regions 410, 412 and multiple (at least two) labeling techniques, the present invention provides a variety of clinical advantages not contemplated or provided in traditional methods, such as traditional ASL-based MR angiography techniques which use only one labeling region and technique.

Specifically, it is contemplated that both continuous (or pseudo-continuous) RF labeling and pulsed (or non-continuous) RF labeling be utilized. As will be further described with respect to FIGS. 4A-4D and by way of example and not limitation, it is contemplated that the first labeling technique applied to the first labeling region 410 may be continuous (or pseudo-continuous). For purposes of discussion, a continuous (or pseudo-continuous) labeling technique will be referred to herein as a substantially continuous labeling technique. That is, even in the case of a pseudo-continuous labeling technique the RF labeling pulses are generally applied every few milliseconds, thereby effectively applying substantially continuous labeling. Continuing with this non-limiting example, it is contemplated that the second labeling technique applied to the second labeling region 412 may be a pulsed or, as will be referred to herein, non-continuous labeling technique. Substantially continuous RF labeling includes applying either a continuous level of RF energy or a train of distinct RF pulses (the latter often referred to as pulsed-continuous or pseudo-continuous RF labeling) to a region containing upstream or inflowing vascular spins. Non-continuous RF labeling (often referred to as pulsed RF labeling) includes applying RF energy in the form of one or a few RF pulses, (usually of the adiabatic type).

As described above, substantially continuous RF labeling provides the advantage of potentially higher resulting SNR in the acquired angiographic images, but with the drawback of reaching SAR limitations, particularly at higher static magnetic field strengths, such as 3T, 7T, and above. In the case of the so-called pseudo-continuous RF labeling techniques that are a subgroup of the above-described substantially continuous RF labeling techniques, the techniques are also limited by the fact that inflowing vascular spins are not labeled after the train of labeling RF pulses ends, which reduces SNR in vascular segments near the labeling region. Additional limitations of traditional pseudo-continuous RF labeling techniques include increased sensitivity to main magnetic field ($B_0$) imperfections, RF field ($B_1$) imperfections, and blood velocity. On the other hand, non-continuous RF labeling results in decreased SNR in the resulting images.

To overcome these competing constraints, the present invention breaks from traditional labeling techniques that generally use a single labeling region and a single labeling technique. As stated above, by way of the illustrated example and not limitation, the first labeling technique applied to the first labeling region 410 is a substantially continuous labeling technique and the second labeling technique applied to the second labeling region 412 is a non-continuous labeling technique. The distinction between the two labeling techniques is reflected in FIGS. 4A-4C by way of the substantially continuous labeling technique illustrated in a cross-hatched pattern of solid lines applied in the first labeling region 410 and the non-continuous labeling technique illustrated in a single-hatched pattern of dotted lines applied to the second labeling region 412.

Figure 4B:
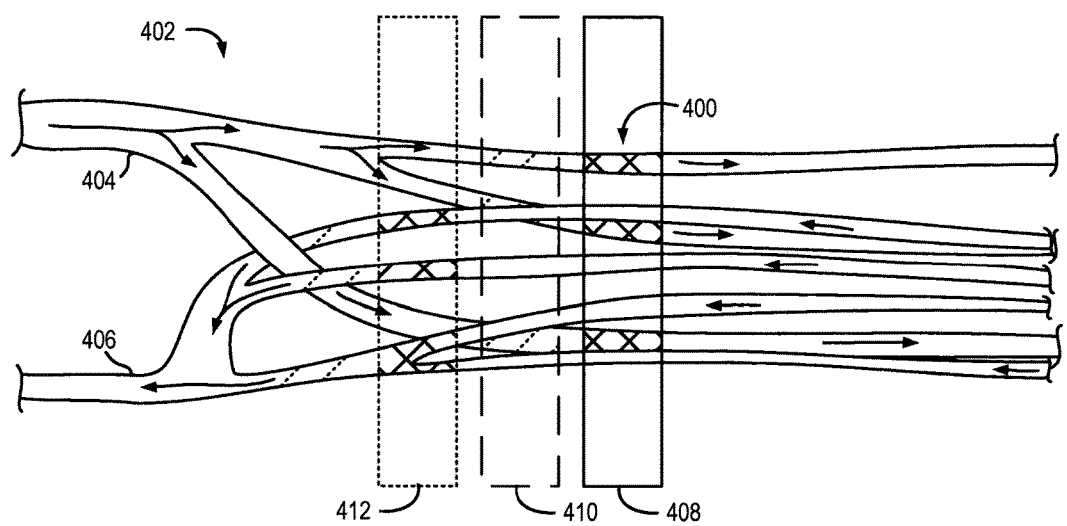

Referring again to FIG. 3, upon completion of the labeling module 302, the imaging module 304 commences with the acquisition of labeled image data from the imaging region 408, as illustrated in FIG. 4B. Specifically, as illustrated in FIG. 4B, as time elapses between the application of the first and second labeling techniques to the first and second labeling regions 410, 412, spins within the vasculature 400 move in the directions indicated by the above-described, superimposed arrows. Thus, spins labeled by the substantially continuous labeling technique applied to the first labeling region 410 in FIG. 4A, move along the arteries 404 into the imaging region 408 and move along the veins 406 into the second labeling region 412, as illustrated in FIG. 4B. Likewise, spins labeled by the non-continuous labeling technique applied to the second labeling region 412 in FIG. 4A, move along the arteries 404 into the first labeling region 410 and move along the veins 406 upstream of the second labeling region 412, as illustrated in FIG. 4B. Accordingly, a delay period may be selected as part of the imaging acquisition either to allow the desired amount of labeled spins to propagate to the imaging region 408, reduce RF energy deposition and SAR, or achieve a preferred image appearance.

Figure 4C:
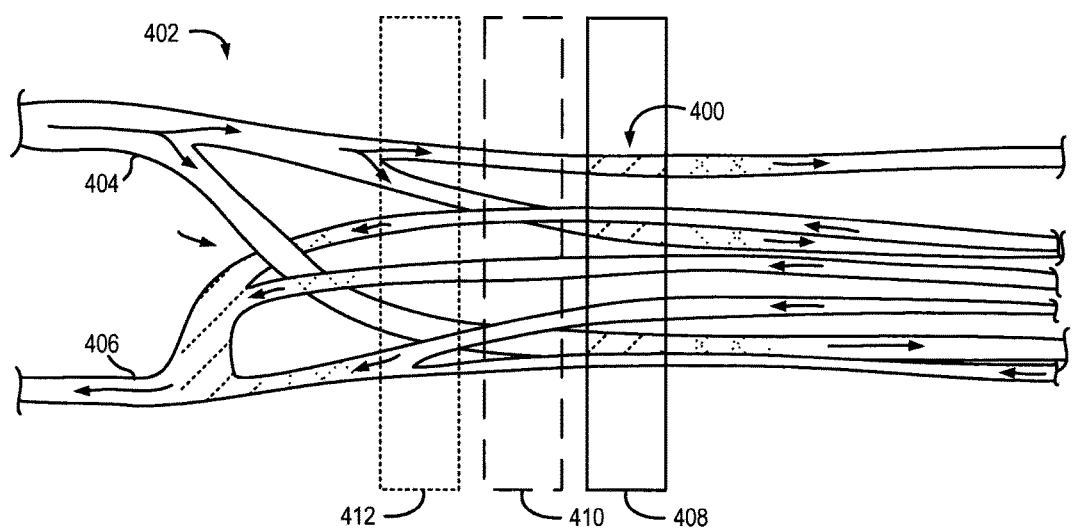

Regardless of whether any delay period is needed or desired, it is contemplated that the acquisition of image data from the imaging region, as indicated in process block 312 of FIG. 3, may extend beyond the duration of the presence of the spins labeled with the substantially continuous labeling technique within the imaging region 408, such as illustrated in FIG. 4C. That is, as illustrated in FIG. 4C, as the imaging acquisition progresses to acquire data from the imaging region 408, the spins labeled by the substantially continuous labeling technique will move along the arteries 404 outside of the imaging region 408 and will move along the veins 406 outside of the second labeling region 412. In addition, as time passes, the bulk magnetization of the labeled spins will relax and the signal attributable to the labeling will decrease. Accordingly, as illustrated in FIG. 4C, the spins labeled with the substantially continuous labeling technique are illustrated by sparsely dotted cross-hatching.

Traditionally, this signal decrease and the bulk movement of the labeled spins from the imaging region 408 would result in a substantially SNR reduction in the images yielded. For example, portions of the arteries 404 located generally on the upstream side of the imaging region may have a lower SNR in the resulting images. However, the present invention overcomes this and the other drawbacks of traditional techniques described above, by the use of a spatially distinct (or at least partially spatially distinct) second labeling region 412 and a second labeling technique, in the described example, a non-continuous labeling technique. That is, as illustrated in FIG. 4C, though the moving spins labeled with the substantially continuous labeling technique have moved from the imaging region 408 and/or have substantially reduced signal, the moving spins labeled with the non-continuous labeling technique have moved along the arteries 404 into the imaging region 408. As also illustrated, the moving spins labeled with the non-continuous labeling technique have moved along the veins 406 downstream of the second labeling region 412. Accordingly, as the imaging acquisition persists, desirable signal is acquired from the moving/labeled spins within the imaging region.

Referring again to FIG. 3, once the acquisition of labeled image data from the imaging region at process block 312 is complete, the process may include the acquisition of non-labeled image data from the imaging region at process block 314. It is noted, however, that this step may occur in a different temporal order and, thus, process block is illustrated in a dotted box. For example, it is contemplated that the acquisition of non-labeled image data from the imaging region may occur in conjunction with performing a planning study at process block 306 or at other times. Regardless of the temporal order of the steps, once the labeled image data and the non-labeled image data is acquired an angiogram is produced, as indicated at process block 316. Specifically, such may be achieved by subtracting the labeled image data and the non-image data to remove stationary spins from the resulting image. Specifically, by way of illustration, it is noted that, although the stationary spins out the arteries 404 and veins 406 are labeled within the first and second labeling regions 410, 412, for ease of understanding, the associated cross- and single-hatching has been foregone from the stationary spins in FIG. 4B and FIG. 4C. Of course, when reconstructing the images to create a desired angiographic image, these stationary or background spins are readily eliminated from the angiographic images by subtraction of the images acquired in conjunction with labeled image data and a non-labeled (or mask) image data. Thus, the conceptual illustrations reflected in FIGS. 4B and 4C are reflective of the imaging information that will ultimately be reflected in the angiographic images produced at process block 316 of FIG. 3.

The present invention improves the SNR and depiction of vascular segments located near the labeling region compared with continuous (or pseudo-continuous) RF labeling. Furthermore, the present invention allows the user to shorten the duration of the continuous (or pseudo-continuous) RF labeling module to reduce RF energy deposition and SAR. Compared with pulsed RF labeling techniques alone, the present invention provides improved signal due to the fact that the SNR advantages of the continuous (or pseudo-continuous) RF labeling technique are included. Additionally, compared with pulsed RF labeling techniques alone, the present invention improves the SNR of vascular segments located near the labeled region because a shorter delay time can be used between the pulsed RF labeling technique and image acquisition.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for acquiring a magnetic resonance angiography (MRA) image of a portion of a vasculature of a subject during one imaging study using a magnetic resonance imaging system, the method comprising:
applying a first labeling pulse sequence to a first labeling region having a first portion of a vasculature of a subject extending through the first labeling region to label spins moving within the first labeling region;
applying a second labeling pulse sequence to a second labeling region having a second portion of a vasculature of the subject extending through the second labeling region to label spins moving within the second labeling region, wherein the first and second labeling pulse sequences include different labeling techniques;
applying an imaging pulse sequence to an imaging region having a third portion of a vasculature of the subject extending through the imaging region that is displaced from the first and second labeling region to acquire imaging data from the spins labeled by the first labeling pulse sequence and the second labeling pulse sequence; and
reconstructing an MRA image of at least the third portion of the vasculature of the subject from the medical imaging data.

2. The method of claim 1 wherein the first labeling region and the second labeling region are discontinuously separate.

3. The method of claim 1 wherein the first labeling region and the second labeling region overlap at least partially.

4. The method of claim 1 wherein one of the first labeling pulse sequence or second labeling pulse sequence includes a non-continuous RF labeling technique and at least one of the first labeling pulse sequence and the second labeling pulse sequence includes a continuous RF labeling technique.

5. The method of claim 1 wherein the first labeling region and the second labeling region are located along an upstream portion of vasculature of the subject with respect to the imaging region.

6. The method of claim 5 wherein the first labeling pulse sequence includes a continuous labeling technique and the second labeling pulse sequence includes a non-continuous labeling technique.

7. The method of claim 5 wherein the first labeling pulse sequence includes a non-continuous labeling technique and the second labeling pulse sequence includes a continuous labeling technique.

8. The method of claim 1 further comprising performing a planning study prior to application of the first labeling pulse sequence to determine at least one of anatomical and physiological parameters of the subject with respect to at least one of the first, second, and third portion of the vasculature of the subject.

9. A magnetic resonance imaging (MRI) system comprising:
a magnet system configured to generate a polarizing magnetic field about at least a portion of a subject arranged in the MRI system;
a plurality of gradient coils configured to apply a gradient field to the polarizing magnetic field;
a radio frequency (RF) system configured to apply an excitation field to the subject and acquire MR image data therefrom;
a computer system programmed to:
apply a first labeling pulse sequence to a first labeling region having a first portion of a vasculature of a subject extending through the first labeling region to label spins moving within the first labeling region;
apply a second labeling pulse sequence to a second labeling region having a second portion of a vasculature of the subject extending through the second labeling region to label spins moving within the second labeling region, wherein the first and second labeling pulse sequences include different labeling techniques;
perform one acquisition module by applying an imaging pulse sequence to an imaging region having a third portion of a vasculature of the subject extending through the imaging region that is displaced from the first and second labeling region to acquire imaging data from the spins labeled by the first labeling pulse sequence and the second labeling pulse sequence; and reconstructing an MRA image of at least the third portion of the vasculature of the subject from the medical imaging data.

10. The system of claim 9 wherein the first labeling region and the second labeling region are discontinuously separate.

11. The system of claim 9 wherein the first labeling region and the second labeling region overlap at least partially.

12. The system of claim 9 wherein one of the first labeling pulse sequence and the second labeling pulse sequence includes a non-continuous RF labeling technique and one of the first labeling pulse sequence and second labeling pulse sequence includes a continuous RF labeling technique.

13. The system of claim 9 wherein the first labeling region and the second labeling region are located along an upstream portion of vasculature of the subject with respect to the imaging region.

14. The system of claim 13 wherein the first labeling pulse sequence includes a continuous labeling technique and the second labeling pulse sequence includes a non-continuous labeling technique.

15. The system of claim 13 wherein the first labeling pulse sequence includes a non-continuous labeling technique and the second labeling pulse sequence includes a continuous labeling technique.

16. The system of claim 9 further comprising performing a planning study prior to application of the first labeling pulse sequence to determine at least one of anatomical and physiological parameters of the subject with respect to at least one of the first, second, and third portion of the vasculature of the subject.

* * * * *